United States Patent [19]

Bieniarz et al.

[11] Patent Number: 5,002,883
[45] Date of Patent: Mar. 26, 1991

[54] COVALENT ATTACHMENT OF ANTIBODIES AND ANTIGENS TO SOLID PHASES USING EXTENDED LENGTH HETEROBIFUNCTIONAL COUPLING AGENTS

[75] Inventors: Christopher Bieniarz, Highland Park; Christopher J. Welch, Urbana; Grady Barnes, Lindenhurst; Carol A. Schlesinger, Wheeling, all of Ill.

[73] Assignee: Abbott Laboratories, Abbott Park, Ill.

[21] Appl. No.: 254,288

[22] Filed: Oct. 11, 1988

Related U.S. Application Data

[63] Continuation-in-part of Ser. No. 114,930, Oct. 30, 1987, abandoned.

[51] Int. Cl.$^5$ .................. C12N 11/06; C07K 17/06
[52] U.S. Cl. .................. 435/176; 435/177; 435/181; 435/188; 435/207; 436/527; 436/532; 530/390; 530/391; 530/405
[58] Field of Search .............. 435/174, 181, 177, 188, 435/176, 7, 21, 28, 207; 530/390, 391, 405; 548/546, 520; 424/85, 91; 436/527, 532; 525/54.1

[56] References Cited

U.S. PATENT DOCUMENTS

| | | | |
|---|---|---|---|
| 4,278,651 | 7/1981 | Hales | 436/532 |
| 4,302,386 | 11/1981 | Stevens | 530/322 |
| 4,459,360 | 7/1984 | Marinkovich | 436/513 |
| 4,581,337 | 4/1986 | Frey et al. | 436/533 |
| 4,582,789 | 4/1986 | Sheldon, III et al. | 435/6 |
| 4,695,624 | 9/1987 | Marburg et al. | 530/395 |
| 4,794,082 | 12/1988 | Sigler | 435/177 |

FOREIGN PATENT DOCUMENTS

| | | | |
|---|---|---|---|
| 0109653 | 5/1984 | European Pat. Off. | 435/174 |
| 0210628 | 2/1987 | European Pat. Off. | 530/403 |
| 0217403 | 4/1987 | European Pat. Off. | 436/524 |
| 0228225 | 7/1987 | European Pat. Off. | 436/523 |
| 62-83665 | 4/1987 | Japan | 436/518 |
| 88/03412 | 5/1988 | World Int. Prop. O. | 530/351 |

OTHER PUBLICATIONS

The Clonentech "Spring 1987 Product Update" brochure.
Fischer et al., *Acta Biol. Med. Germ.*, Band 36, pp. 999–1005 (1972).
Freytag et al., *Clinical Chemistry*, 30(9):1494–1498 (1984).
Imagawa et al., *Journal of Applied Biochemistry*, 4:41–57 (1982).
Kato et al., *Rinsho Kagaku Shimpojumu*, No. 16, pp. 10–14 (1976).
Kato et al., *Igaku No Ayumi*, 104(12):805–807 (1978).
Keller, et al., *Helvetica Chimica Acta*, 58:531–541 (1975).
Kitigawa, et al., *Chem. Pharm. Bull.*, 29(4):1130–1135 (1981).
Manecke, et al., *Biochemie*, 62:603–613 (1980).
Yoshitake, et al., *Analytical Letters*, 15(B2):147–160 (1982).
Yoshitake, et al., *Europ. J. Biochem.*, 101:395–399 (1979).
Yoshitake, et al., *J. Biochem.*, 92(5):1413–1424 (1982).

*Primary Examiner*—Margaret Moskowitz
*Assistant Examiner*—Kay Kim
*Attorney, Agent, or Firm*—Richard D. Schmidt; Daniel W. Collins; Thomas M. Breininger

[57] ABSTRACT

Novel methods for covalent attachment of antibodies, antigens, or other molecules to solid phases using extended length heterobifunctional crosslinking reagents are disclosed. The resulting derivatized solid phases can be used in diagnostic assays.

8 Claims, No Drawings

COVALENT ATTACHMENT OF ANTIBODIES AND ANTIGENS TO SOLID PHASES USING EXTENDED LENGTH HETEROBIFUNCTIONAL COUPLING AGENTS

This application is a continuation in part of U.S. patent application Ser. No. 114,930 filed Oct. 30, 1987, now abandoned, entitled Heterobifunctional Couplinq Agent which is incorporated herein by reference.

BACKGROUND OF THE INVENTION

The present invention relates to a method for covalent attachment of antibodies or other molecules to a solid support using extended length heterobifunctional reagents.

In diagnostic assays, the reaction between a specific binding member and its complement is often employed to detect whether (and in some assays, how much) specific binding member or complement is present in a sample. In one type of diagnostic assay, a specific binding member (e.g. an antibody) is detected in a sample by introducing its complement (e.g. an antigen) into the sample and determining if any reaction occurs between the two reagents. Alternatively, the complement itself can be detected in a sample by introducing the specific binding member into the sample and determining whether any reaction occurs. Because it is often difficult to detect whether any reaction has occurred, a second specific binding member may be added to the sample. The second specific binding member can react either with the first specific binding member or its complement, and the second member bears a detectable label. Of course, it is impossible to determine beforehand how much labelled second specific binding member must be added because it is unknown how much, if any, of the substance to be detected is in the sample. Thus, the labelled specific binding member is added in excess of the maximum concentration of the substance typically found in such samples. However, the labelled specific binding member which does not bind with the substance must be separated from the sample so that only the bound labelled member is detected, indicating that the substance is indeed in the sample.

A common approach to separate bound from unbound labelled member is to employ solid phase separation. A typical example of such separation involves linking the first specific binding member (in the case of assays for complement to the first member) or complement (in the case of assays for specific binding member) to a solid phase (such as microparticles) which can be separated from the sample, for example, by filtration or gravity sedimentation. The label associated either with the solid phase or still in the sample is proportional to the amount of substance to be detected in the original sample.

Other variations to this general solid phase separation scheme have been developed, but most such schemes involve the binding of the substance to be analyzed to a specific binding member linked to a solid phase. This binding is crucial to assay performance. However, the linkage between the solid phase and the specific binding member can subsequently affect binding of the substance to be analyzed. An example will illustrate the point. Antibodies have extremely specific structural, spacial, and polar configurations which endow them with the ability to recognize and bind to one type of analyte, and virtually none other. When antibodies are employed in assays for the detection of antigens, antibodies can be linked to solid phases. However, the proximity of the solid phase to the antibody can block sites on the antibody where antigen binds. Alternatively, the linkage (usually covalent) between the antibody and solid phase can alter the structure (conformation) of the antibody so that the linkage may deleteriously affect binding of the antibody to the analyte. The same situation holds for conjugation of analytes, particularly proteins, to solid phases. The analyte conformation can change upon conjugation so the free antibody in the sample can no longer recognize it.

Covalent attachment of proteins to solid phases using heterobifunctional reagents has been accomplished with mixed results in the past. In some cases the proteins were directly conjugated to the solid phase. Generally, the connecting tether has been quite short in comparison with the size of the bound protein. This is disadvantageous in that the bound protein can still be hindered in performing its biological function due to steric crowding, inaccessability of binding sites, etc. This has been a problem which has limited the bioactivity and stability of derivatized solid phases in the past.

SUMMARY OF THE INVENTION

This invention involves conjugates of solid phases with novel linking groups which can be used to link solid phases to substances such as proteins, antibodies, antigens and the like. These conjugates are hydrophilic, so they tend to be quite stable in aqueous solutions, and they preserve the conformation of such substances when such substances are linked to solid phases. At the same time, these linking groups are of such lengths that the solid phases tend not to interfere with binding sites on such substances.

This invention involves chemically derivatized solid phase materials of the formula:

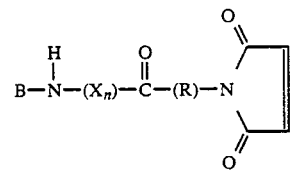

wherein B is an amine bearing solid phase material; X is a substituted or unsubstituted amino acid having from three to ten carbon atoms in a straight chain; n is from one to ten; and R is an alkyl, cycloalkyl, an alkylcycloalkyl or an aromatic carbocyclic ring.

The current invention also involves protein-solid phase conjugates of the formula:

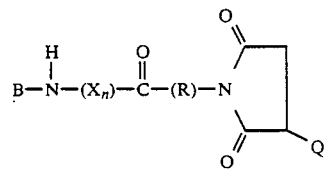

wherein Q is a SH or a thiol bearing peptide polypeptide or protein: and wherein B, X. n, and R are as defined previously.

DETAILED DESCRIPTION OF THE INVENTION

As indicated above, the present invention involves conjugates of "amine bearing solid phases." Such solid phases include those polymers, glasses, and natural products which bear amine (either primary, secondary, or tertiary) groups which can be reacted with a maleimide moiety to form a stable covalent bond. A wide variety of solid phases are possible, consistent with this definition: commercially available polystyrene aminated particles, amino silica gels, partially hydrolyzed nylon, partially reduced polyacrylamides, partially reduced cyanoacrylates and copolymers containing such polymers. Solid phases containing nitrile groups which can be reduced to yield amine groups to produce "amine-bearing solid phases" consistent with this invention.

While the Examples which follow generally deal with microparticle solid phases, other solid phase configurations are possible: beads, sheets, spheres, filters, and the like. However, one solid phase configuration of particular interest is fibers. Many of the polymers mentioned previously are available in fiberous form. These fibers can be chopped (discontinuous) or continuous, but the latter are preferred. Continuous fibers can be derivitized with the linking groups of this invention, and proteins such as antibodies can be conjugated to the linking groups. The protein-bearing fiber can then be sewn or woven into a solid support such as cloth, a mat, or a woven or non-woven filter media. The fiber can be sewn or woven into distinctive patterns. For example, the fibers can be arranged in a plus (+) sign with the vertical bar having positive controls and the horizontal bar having negative controls, as disclosed in copending U.S. application Ser. No. 831,013 which is incorporated herein by reference. Thus, when an assay is performed using the sewn fibers, a plus sign will appear if the sample passed through the media has analyte in it, and a minus (−) (horizontal bar only) will appear if no analyte is in the sample.

Another approach is to attach the linking groups of this invention to the fiber, sew the fiber into an inert backing material (i.e. a material which lacks maleimide groups), and react the protein to the exposed maleimide moieties on the linking groups.

The term "alkyl-cycloalkyl" as used herein includes alkyl groups linked to cycloalkyl ring structures where the alkyl group links the cycloalkyl to the maleimide or the carbonyl groups in the chemical structures shown above. The term "alkyl" includes straight or branched alkyl groups, preferably lower alkyl groups having from one to six carbon atoms.

The substituent "Q" is a —SH or thiol-bearing peptide, polypeptide or protein. For convenient reaction with the linking groups of this invention, the peptide, polypeptide or protein to be conjugated to the linking groups bear reactive thiol (mercapto) or sulfhydryl (—SH) groups. It is recognized that mercapto groups contain sulfhydryl groups, but this invention contemplates that peptides, polypeptides or proteins lacking sulfhydryl groups may be artificially derivatized with sulfhydryl groups which are not mercapto groups, mercapto groups being organic compounds bearing sulfhydryl groups. The sulfhydryl group on the peptide, polypeptide or protein reacts with maleimide moiety on the linking groups of this invention to form a covalent bond between the linking groups and the peptide, polypeptide or protein.

The Examples which follow illustrate this invention. Examples 1-6 describe the synthesis of various linker groups of this invention. Examples 7-18 describe the uses of the linker groups to conjugate solid phases to proteins. These examples are not intended to limit the invention.

Example 1

Synthesis of:

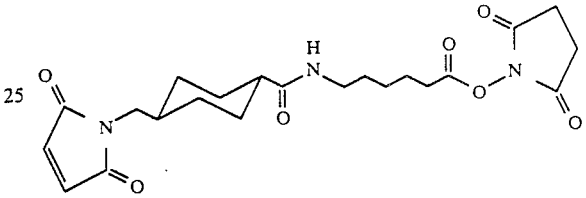

Trans-4-(aminomethyl)-cyclohexanecarboxylic acid was purchased from Aldrich Chemical Co. and converted to N-(4-carboxycyclohexylmethyl) maleimide N-Hydroxysuccinimide active ester by the method of Yoshitake et al. (*J. Biochem.*, 101:395-399 (1979)). This material (100 mg) is then dissolved in dry dimethylformamide (DMF) (1.0 ml), 6-aminocaproic acid (39.2 mg; 1.0 eq) is added, and the resulting mixture is stirred overnight at room temperature under nitrogen atmosphere. The following morning dicyclohexylcarbodiimide (DCCI) (67.8 mg; 1.1 eq) is added, and the reaction mixture is stirred for an additional six hours. Precipitated dicyclohexylurea (DCU) is removed by filtration, and the resulting DMF solution is evaporated under reduced pressure to give a tacky solid, which is purified by flash chromatography upon silica gel (5% methanol/chloroform) to give compound 1 (71 mg) as a white solid in 53% overall yield. (R=cyclohexylmethyl; n=1; X=6-aminocaproyl).

Example 2

Synthesis of:

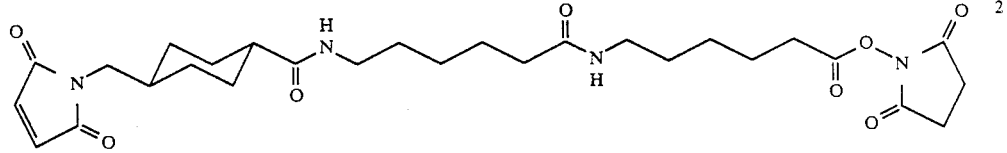

Compound 1 (100 mg; synthesis described in Example 1) is dissolved in dry DMF (1.0 ml), 6-aminocaproic acid (29.3 mg; 1.0 eq) is then added and the resulting mixture is stirred overnight at room temperature under nitrogen atmosphere. The following morning DCCI (50.7 mg; 1.1 eq) is added, and the reaction mixture is stirred for an additional six hours. Solid precipitate (DCU) is removed by filtration, and the resulting DMF solution is evaporated under reduced pressure to give a tacky solid, which is purified by flash chromatography upon silica gel (10% methanol/chloroform to give compound 2 (60 mg) as a white solid in 48% overall yield. (R=cyclohexylmethyl; n=2; X=6-aminocaproyl).

Example 3

Synthesis of:

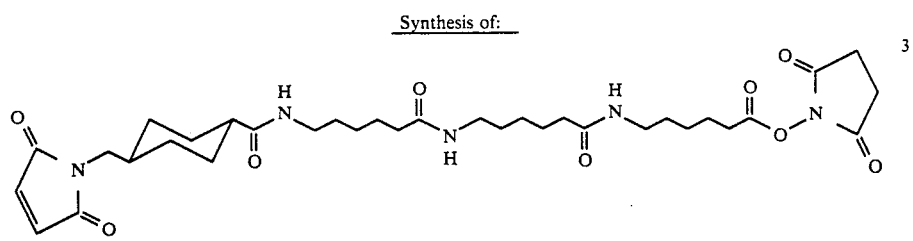

Compound 2 (100 mg; Gynlhesis described in Example 2) is dissolved in dry DMF (2.0 ml), 6-aminocaproic acid (23.4 mg; 1.0 eq) is then added, and the resulting mixture is stirred overnight at room temperature under nitrogen atmosphere. The following morning, DCCI (40.5 mg; 1.1 eq) is added, and the reaction mixture is stirred for an additional six hours. Solid precipitate (DCU) is removed by filtration, and the resulting DMF solution is evaporated under reduced pressure to give a tacky solid, which is purified by flash chromatography upon silica gel (10% methanol/chloroform) to give compound 3 (60.0 mg) as a white solid in 50% overall yield. (R=cyclohexylmethyl; n=3; X=6-aminocaproyl).

Example 4

Synthesis of:

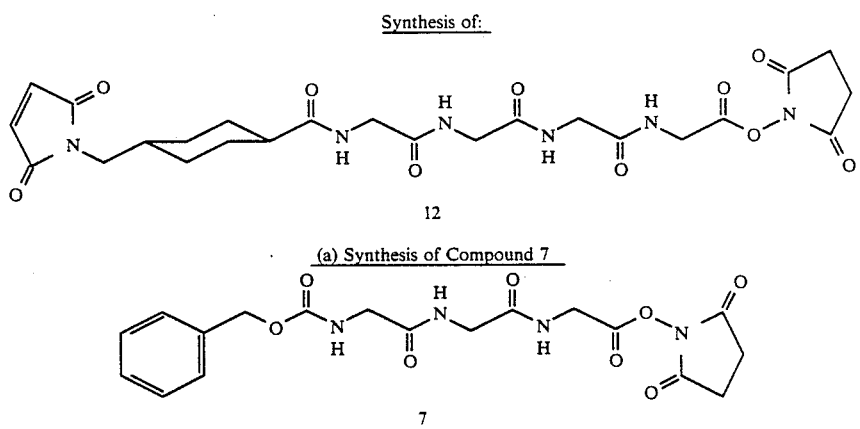

Compound 3 (100 mg; synthesis described in Example 3) is dissolved in dry DMF (10.0 ml), 6-aminocaproic acid (19.5 mg; 1.0 eq) is then added, and the resulting mixture is stirred overnight at room temperature under nitrogen atmosphere. The following morning DCCI (33.7 mg; 1.1 eq) is added, and the reaction mixture is stirred for an additional six hours. Solid precipitate (DCU) is removed by filtration, and the resulting DMF solution is evaporated under reduced pressure to give a tacky solid, which is purified by flash chromatography upon silica gel (10% methanol/chloroform) to give compound 4 (53 mg) as a white solid in 45% overall yield. (R=cyclohexylmethyl; n=4; X=6-aminocaproyl).

Example 5

Synthesis of:

12

(a) Synthesis of Compound 7

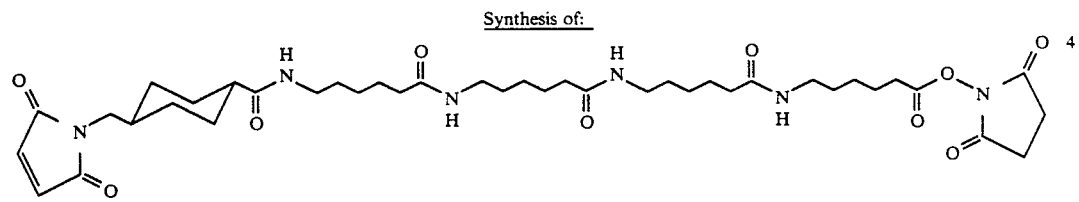

CBZ-triglycine (4.0 g; Bachem Chem. Co.) is dissolved in 50.0 ml dry DMF. N-hydroxysuccinimide (1.42 g; 1.0 eq), and DCCI (2.55 g; 1.0 eq) are added and the resulting mixture is stirred overnight at room temperature under nitrogen atmosphere. The following morning, precipitated DCU is removed by filtration, and the resulting DMF solution is evaporated under reduced pressure to give a yellow oil. Recrystallization from ethyl acetate/chloroform gives the intermediate compound 7 (3.0 g) in 57% yield.

(b) Synthesis of Compound 8

8

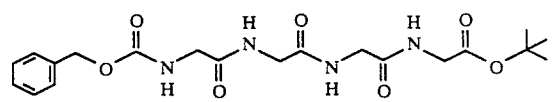

Glycine t-butyl ester hydroxhloride (0.54 g; Sigma Chem. Co.) is suspended in dry DMF (25.0 ml). Compound 7 (1.35 g; 1.0 eq) from Part (a) is then added, along with triethylamine (1.62 g; 5.0 eq). The resulting solution is allowed to stir overnight at room temperature under nitrogen atmosphere. The following morning, solvent is removed under reduced pressure to give a crude product. Recrystallization from ethyl acetate/chloroform gives intermediate compound 8 (0.95 g) in 68% yield.

(c) Synthesis of Compound 9

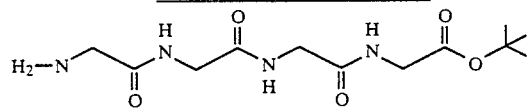

Compound 8 (0.95 g) from Part b is dissolved in dry methanol (300 ml). Glacial acetic acid (0.45 ml) is then added and the solution is purged with nitrogen for 15 minutes. Palladium on carbon (1.5 g; palladium content 10%) is then carefully added, with stirring. A stream of hydrogen gas is bubbled through the stirring solution for three hours at room temperature. The solution is carefully purged with nitrogen for 15 minutes, then filtered. The filtrate solution is concentrated under reduced pressure to give intermediate compound 9 (700 mg) as the acetate salt.

(d) Synthesis of Compound 10

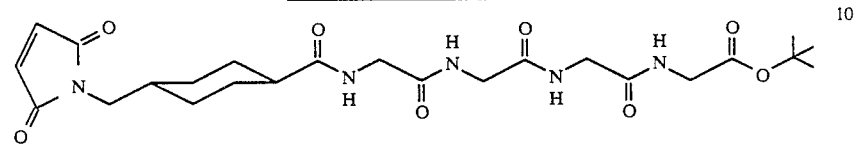

Compound 9 (700 mg: acetate salt) from Part c is dissolved in dry DMF (25 ml). N-(4-carboxycyclohexylmethyl)maleimide (697 mg) from Example 1 is then added, and the mixture is allowed to stir overnight at room temperature under nitrogen atmosphere. The following morning DMF is evaporated under reduced pressure to afford a crude product. Recrystallization from ethyl acetate/hexane affords intermediate compound 10 in 22% yield.

(e) Synthesis of Compound 11

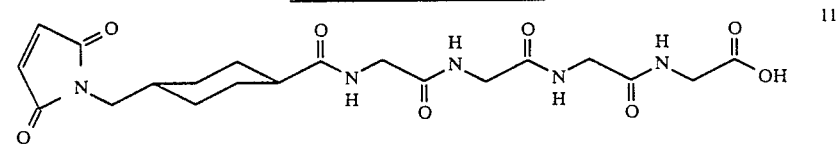

Compound 10 (225 mg) from Part d is suspended in chloroform (1.5 ml). Dry trifluoroacetic acid (1.5 ml) is then added, and the mixture is stirred at room temperature under a nitrogen atmosphere for a period of three hours. Solvent is evaporated under reduced atmosphere to give a crude product. Trituration with ethyl acetate gives intermediate compound 11 (127 mg) in 61% yield.

(f) Synthesis of Compound 12

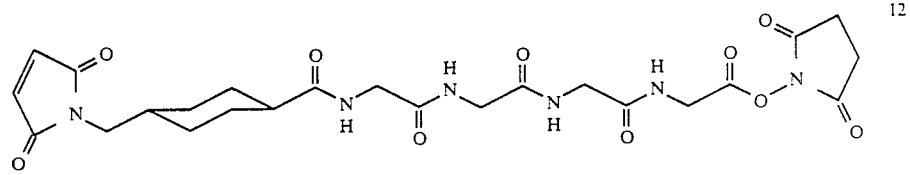

Compound 11 (100 mg) from Part e is dissolved in dry DMF (7.0 ml) along with N-hydroxysuccinimide (37.1 mg; 1.5 eq) and DCCI (221.5 mg; 5.0 eq). The reaction mixture is stirred overnight at room temperature under a nitrogen atmosphere. The following morning, precipitated DCU is removed by filtration, and DMF is evaporated under reduced pressure to give a crude solid. Trituration with chloroform gives compound 12 (86 mg) in 60% yield. (R=cyclohexylmethyl; n=4; X=glycyl).

Compound 12 can be used for conjugating proteins (e.g. antibody and enzymes) to solid phases using the procedures outlined in the following Examples.

Example 6

Synthesis of m-Maleimidobenzoylcaproamido-N-Hydroxy Succinimide

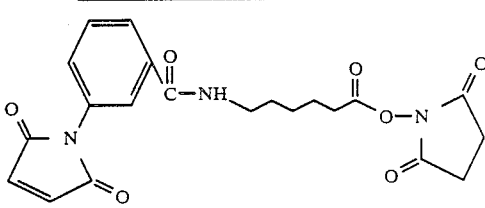

A round bottom flask equipped with a magnetic stirrer is charged with m-maleimidobenzoyl-N-hydroxysuccinimide ester (0.314 g; 0.001 mole) obtained from Pierce Corporation dissolved in DMF (5.0 mL). 6-Aminocaproic acid (0.131 g; 1 equiv.) is added, and the resulting solution is stirred overnight at room temperature under nitrogen. After 18 hours, olicyclohexylcarbodiimide (DCCI; 0.206 g; 1.1 equiv.) is added followed by N-hydroxysuccinimide (0.115 g, 1 equiv.). The reaction solution is stirred for additional eight hours at room temperature under nitrogen. Precipitated dicyclohexylurea (DCU) is removed by filtration, and the resulting DMF solution is evaporated under reduced pressure. The resulting solid is purified by silica gel chromatography (5% methanol in chloroform) to give compound 13 in 50% yield. This compound is treated with aminocaproic acid in a manner identical to the method described in examples 2, 3 and 4 of this application to produce compounds where n is up to ten, and R=phenyl).

Example 7

Preparation of Monoclonal anti-CA-125 IgG-Derivatized Microparticles using a 30 Atom Linkage (a) Pretreatment of Amine Microparticles Amine microparticles (Seradyn; 0.164 micron; 2.5% solids; 1 ml) are mixed with 0.5 g Biorex ion exchange resin (Biorex MSZ501D; 20–50 mesh; catalog #142-7425). The mixture is rotated end-over-end for one hour at room temperature, then vacuum filtered through a course sintered glass funnel with washing. The filtrate is collected and centrifuged at 15,000 rpm for 30 minutes. Supernatant is discarded, and the microparticle pellet is resuspended in distilled water with vortexing, and adjusted to 2.5% solids by addition of distilled water.

(b) Derivatization of the Particles

Resuspended, pre treated particles from part a at 2.5% solids are mixed with an equal volume of compound 3 (Example 3) solution (2 mg/ml in DMF) and allowed to react at room temperature for one hour with end-over-end rotation. The reaction mixture is then diluted ten-fold with phosphate-buffered saline "PBS" (pH 7.2), and centrifuged at 15,000 rpm for 30 minutes. The resulting supernatant is discarded, and the microparticle pellet is resuspended with phosphate-buffered saline. The centrifugation-resuspension sequence is repeated twice, the solution is again centrifuged, supernatant is discarded, and the pellet is resuspended to a concentration of 2.5% solids with Tris buffer (0.05 M tris; 0.1 M NaCl; pH 8.0).

(c) Preparation of the Antibody

A solution of monoclonal anti-CA-125 IgG (7.4 mg/ml; in phosphate-buffered saline) is incubated with DTT (dithiothreitol; 25 mM in final reaction mixture) for twenty minutes at room temperature with stirring on a rotary agitator. The solution of partially reduced antibody is then desalted by chromatography upon a pre-equilibrated Sephadex G-25 (coarse) column with pH 7.0 phosphate buffer (0.1 M phosphate; 0.1 M NaCl, 5 mM EDTA) as eluent. Fractions are collected, protein-containing fractions are pooled, and the protein concentration of the pooled solution is estimated by measuring absorbance at 280 nm.

(d) Reaction of Maleimide-Derivatized Microparticles with Partially Reduced IgG

The partially reduced antibody from part c (1 ml; 1 mg/ml) is combined with the maleimide-derivatized microparticles from part (b) (1 ml; 2.5% solids). The mixture is rotated end over end at room temperature overnight. The following morning, the reaction mixture is diluted ten-fold with wash buffer (0.01 M phosphate; pH 7.2; 1% Tween), then centrifuged at 15,000 rpm for 30 minutes. The resulting supernatant is discarded, the microparticle pellet is washed twice (vortexing in 1 ml wash buffer; diluting tenfold with wash buffer, then centrifuging at 15,000 rpm for 30 minutes followed by discarding supernatant). The washed pellet is resuspended to a final concentration of 0.125% solids in storage buffer (0.01 M Tris; pH 8.1; 0.1 M NaCl; 0.1% sodium azide; 13.6% sucrose). The final microparticle suspension is first passed through a 23, then a 25 gauge needle. The resulting microparticle conjugate has the anti-CA-125 IgG antibody conjugated to the microparticle with a 30 atom linker arm from Example 3. Microparticles in storage buffer are stored until future use in an immunoassay for the detection of CA-125 antigen.

Example 8

Preparation of Monoclonal anti-CA-125 IgG-Derivatized Microparticles using a 23 Atom Linkage The procedure of Example 7 is repeated using the 23 atom linker group (Compound 2) from Example 2 instead of the 30 atom group of Example 7.

Example 9

Preparation of Monoclonal anti-CA-125 IgG-Derivatized Microparticles using a 16 Atom Linkage The procedure of Example 7 is repeated using the 16 atom linker group (Compound 1) from Example 1 instead of the 30 atom group of Example 7.

Example 10

Preparation of Polyclonal anti-CA-125 IgG-Derivatized Microparticles using a 30 Atom Linkage The procedure of Example 7 is repeated using a polyclonal anti-CA-125 IgG antibody instead of the monoclonal antibody of Example 7. Polyclonal anti-CA-125 antibody was obtained by immunizing sheep subcutaneously and intramuscularly with 50,000 units of CA-125 antigen in Freund's adjuvant. All subsequent boosts were done every two weeks using 50,000 units of CA-125 antigen in Freund's incomplete adjuvant.

Example 11

Preparation of Monoclonal anti-PAP IgG-Derivatized Microparticles using a 30 Atom Linkage (a) Preparation of Reduced anti-PAP antibody Dithiothreitol (DTT; 1.93 mg) is placed in a reaction vial. Mouse monoclonal anti-PAP antibody (0.5 ml; 6.98 mg/ml) is then added, and the mixture is uncubated at room temperature for 20 minutes at room temperature. The reaction mixture is then applied to a pre-equilibrated Sephadex G-25 column (coarse 1×20 cm) and eluted with pH 7.2 phosphate buffer (0.2 M phosphate; 0.1 M NaCl; 5.0 mM EDTA). Fractions are collected and absorbance at 280 nm is measured. Protein-containing fractions are combined, the pool is diluted ten-fold with chromatography buffer, and protein concentration of the resulting diluted pool of activated antibody is estimated by measuring absorbance at 280 nm.

(b) Reaction of Derivatized Microparticles with Reduced Anti-PAP Antibody

Reduced antibody from part a (0.5 mg (e.g. 336 ul at 1.49 mg/ml)) is placed in a reaction vial. The derivatized microparticle solution (0.5 ml) from Example 7 part b is then added, and the mixture is incubated overnight at room temperature on a rotary agitator. The following morning, the reaction mixture is centrifuged (20 minutes at 12,000 rpm), supernatant is removed, and absorbance at 280 nm is measured. The antibody-derivatized microparticles are then resuspended in PBS-Tween buffer (0.1 g Tween in 100 ml PBS; 1.0 ml). The mixture is again centrifuged (20 minutes at 12,000 rpm), supernatant is discarded, and 5.0 ml storage buffer (0.01 M Tris; 0.1 M NaCl; 0.1% sodium azide; 13.6% sucrose; pH 8.1) is then added. The microparticles are passed first through a 23 gauge needle, then a 25 gauge needle. The resulting microparticle suspension is then transferred to a 10 ml plastic screw-cap vial for storage until use in an enzyme immunoassay for the detection of PAP antigen.

Example 12

Covalent Attachment of B-12 Intrinsic Factor to Aminated Polystyrene Microparticles A 10% solution of 100 ul of aminated polystyrene microparticles (0.164 micron, purchased from Seradyn) is placed in a reaction vial. A solution of Compound 2 in DMF (9 ul; 1.21 mM) is added with a solution of B-12 intrinsic factor (210 ul; 0.1537 mg/ml) in phosphate-buffered saline. The reaction mixture is rotated end-over-end overnight at room temperature. The following morninq, the reaction mixture is centrifuged (30 minutes; 13,000 rpm). Supernatant is discarded, the remaining solid is resuspended in distilled water, and the centrifuging-resuspension step is repeated.

The product produced is a B-12 intrinsic factor/microparticle conjugate linked with a 23 atom linker of Example 2. The particles are then suspended in 750 ul of buffer (0.01 M Tris; 0.1 M NaCl; 0.1% sodium azide; 13.6% sucrose; pH 8.1) and used in an assay for the detection of B-12.

Example 13

Covalent Attachment of Recombinant Hepatitis B Core Antigen to Aminated Polystyrene Microparticles Using Compound 3

(a) Derivitization of Microparticles with Compound 3

Amino microparticles (Polysciences; 0.5 micron) are placed in a reaction vial. A solution of Compound 3 (Example 3) in DMF is then added, and the mixture is treated as described in Example 7 part b.

(b) Reaction of Recombinant Core Antigen With Derivatized Microparticles

Recombinant hepatitis B core antigen is placed in a vial. Derivatized microparticles (from part a) are then added, and the mixture is treated as described in Example 7 part d to yield microparticles conjugated to the antigen with a 30 atom linker which can be used in assays for detection of hepatitis B.

Example 14

Preparation of E. coli β-Galactosidase-Derivatized Microparticles With A 30 Atom Linkage E. coli β-galactosidase (1 ml; 1 mg/ml) in pH e buffered saline (0.M phosphate; 0.1M 7.0 phosphate buffered saline (0.1 M phosphate; 0.1 M NaCl) is added to maleimide-derivatized microparticles from Example 7, part b. The reaction mixture is rotated end-over-end overnight at room temperature. The following morning the reaction mixture is centrifuged at 15,000 rpm for 30 minutes. The resulting supernatant is discarded, and the microparticle pellet is resuspended to 2.5% solids with pH 7.0 phosphate buffered saline (0.M phosphate; 0.M NaCl). The centrifugation, decanting, resuspension sequence is repeated twice. The microparticle pellet is finally resuspended in storage buffer (0.1 M tris; pH 7.0; 0.1 M NaCl; 0.1% sodium azide; 13.6% sucrose). The resulting microparticle suspension is passed through first a 23, then a 25 gauge needle. The product is E. coli β-galactosidase conjugated to amino microparticles with a 30 atom linkage. Enzyme-derivatized microparticles in storage buffer are then stored until future use.

Example 15

Preparation of Calf Intestinal Alkaline Phosphatase-Derivatized Microparticles Using a 30 Atom Linkage (a) Thiolation of the Enzyme Calf intestinal alkaline phosphatase (0.5 ml; 10 mg/ml) in pH 8.0 Tris buffer (0.05 M Tris; 10 mM $MgCl_2$; 0.1 mM $ZnCl_2$) is placed in a reaction vial. Iminothiolane hydrochloride is then added to a concentration of 4.0 mM. The mixture is stirred for 30 minutes at room temperature, then desalted on a Sephadex G-25 (coarse) column with phosphate-buffered saline (0.1 M phosphate; 0.1 M NaCl; 10 mM $MgCl_2$, 0.1 M $ZnCl_2$; pH 7.0) as eluent. Fractions are collected, protein-containing fractions are pooled, and protein concentration of the pooled solution of thiolated enzyme is estimated by measuring absorbance at 280 nm.

(b) Reaction of Thiolated Enzyme with Maleimide Derivatized Microparticles

Thiolated enzyme from part a (1 ml; 1 mg/ml) is combined with the maleimide-derivatized microparticles from Example 7, part b (1 ml; 2.5% solids). The reaction mixture is rotated end-over-end overnight at room temperature, then treated as described in Example 7, part d to provide a suspension of microparticles covalently derivatized with calf intestinal alkaline phosphatase.

Example 16

Preparation of Monoclonal Anti-CA-125 IgG-Derivatized Microparticles (a) Preparation of Thiolated Microparticles Resuspended, pretreated amine microparticles from Example 7, part a (1 ml; 2.5% solids) are mixed with iminothiolane HCl to achieve a final iminothiolane concentration of 50 mM. The reaction mixture is stirred at room temperature for one hour, then treated as described in Example 7, part b.

(b) Derivatization of the Antibody

A solution of monoclonal anti-CA-125 IgG (7.4 mg/ml) in phosphate buffered saline is incubated with 30 molar equivalents of a DMF solution of Compound 3 (5.0 mM). The reaction mixture is stirred for 30 minutes at room temperature, then desalted on a Sephadex G-25 (coarse) column with pH 7.0 phosphate buffer (0.1 M phosphate; 0.1 M NaCl) as eluent. Fractions are collected, protein-containing fractions are pooled, and protein concentration of the pooled solution is estimated by measuring absorbance at 280 nm.

(c) Reaction of Thiolated Microparticles with Maleimide-Derivatized Antibodies

Thiolated microparticles from part a (1 ml; 2.5% solid) are mixed with maleimide-derivatized antibodies from part (b) (1 ml; 1 mg/ml). The reaction mixture is rotated end-over-end overnight at room temperature. The following morning, the antibody-derivatized microparticles are treated as described in Example 7, part (d) to produce a microparticle/IgG conjugate which can be used in an assay for the detection of CA-125 antigen.

Example 17

Preparation of Monoclonal anti-CA-125 IgG-Derivatized Nylon Fibers (a) Pretreatment of Nylon Fibers Nylon monofilement fishing line (Berkley, 6 inches, 2 lb. test) is incubated for 30 minutes at room temperature with 3N HCl (10 ml) with shaking. The fiber is then washed twice with 20 ml distilled water. The washed, partially hydrolyzed fiber is stored in distilled water until further use.

(b) Maleimide Derivitization of Partially Hydrolyzed Nylon Fiber

A two inch section of partially hydrolyzed nylon fiber from part (a) is cut into ⅛ inch pieces. The ⅛ inch nylon lengths are placed in a reaction vial along with a DMF solution of Compound 3 (1.0 ml; 5.0 mM). The reaction mixture is shaken vigorously for two hours, then filtered through a course sintered glass funnel. The maleimide-derivatized nylon fibers are washed several times with distilled water, then stored until further use in distilled water.

(c) Reaction of Maleimide-Derivatized Nylon Fibers with Partially Reduced anti-CA-125 IgG Partially reduced monoclonal anti-CA-125 IgG from Example 7, part (c) (1 ml; 1 mg/ml) is added to maleimide-derivatized nylon fibers from part b. The reaction mixture is incubated overnight at room temperature with end-over-end rotation. The following morning, the reaction mixture is filtered through a coarse sintered glass funnel and the antibody-derivatized fibers are washed several times with wash buffer (0.1 M phosphate; 0.1 M NaCl; pH 7.0). The resulting fibers contain covalently attached monoclonal anti-CA-125 IgG via a 30 atom spacer group. The resulting fibers are stored in fiber storage buffer (0.1 M, phosphate; 0.1 M NaCl; 1% BSA; 0.1% sodium azide) for use in an assay for the detection of CA-125 antigen).

Example 18

Preparation of Monoclonal anti-CA-125 IgG-Derivatized Wool Fibers (a) Partial Reduction of Wool Thread Wool thread is cut into ½ inch pieces. A piece of thread is then immersed in 1 ml 5 mM DTT solution and shaken vigorously for one hour. The reaction mixture is then filtered through a coarse sintered glass funnel, and washed five times with buffer (pH 7.0; 0.1 M phosphate; 0.1 M NaCl; 5 mM EDTA).

(b) Reaction of Maleimide-Derivatized Antibody With Partially Reduced Wool Thread Partially reduced wool thread from part a is placed in a reaction vial. Maleimide-derivatized monoclonal anti-CA-125 IgG from Example 7, part d (1 ml; 1 mg/ml) is then added, and the mixture is rotated end-over-end overnight at room temperature. The following morning, the reaction mixture is filtered through a coarse sintered glass funnel and washed five times with wash buffer (0.1 M phosphate; 0.1 M NaCl; pH 7.0). The resulting fiber contains monoclonal anti-CA-125 IgG covalently attached via a 30 atom spacer group. The resulting fibers are stored in fiber storage buffer (0.1 M phosphate; 0.1 M NaCl; 1% bovine serum albumin; 0.1% sodium azide) until used in an assay for the detection of CA-125 antigen.

What is claimed is:

1. A conjugate of the formula

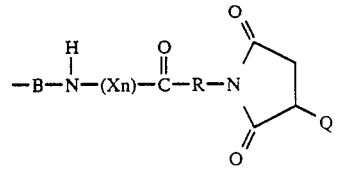

wherein Q is a thiol bearing peptide, polypeptide or protein; B is an amine bearing solid phase material; X is an amino acid having from three to ten carbon atoms in a straight chain; n is from one to ten; and R is a cycloakyl or an aromatic carbocycle ring.

2. The conjugate of claim 1 wherein R is cyclohexylmethyl.

3. The conjugate of claim 1 wherein B is an amine bearing microparticle.

4. The conjugate of claim 1 wherein X includes aminocaproyl.

5. The conjugate of claim 1 wherein Q is selected from the group of a hepatitis antigen, an enzyme, or an antibody.

6. The conjugate of claim 5 wherein said enzyme is selected from beta-galactosidase.

7. The conjugate of claim 5 wherein said antibody is selected from an anti-CA 125 antibody.

8. The conjugate of claim 5 wherein said hepatitis protein is selected from hepatitis B core antigen.

* * * * *